(12) United States Patent
Murray

(10) Patent No.: US 9,354,157 B2
(45) Date of Patent: May 31, 2016

(54) APPARATUS AND METHOD FOR ASSESSING SUBGRADE CORROSION

(71) Applicant: Electric Power Research Institute, Inc., Charlotte, NC (US)

(72) Inventor: Neal Scott Murray, Charlotte, NC (US)

(73) Assignee: Electric Power Research Institute, Inc., Charlotte, NC (US)

(*) Notice: Subject to any disclaimer, the term of this patent is extended or adjusted under 35 U.S.C. 154(b) by 135 days.

(21) Appl. No.: 14/143,103

(22) Filed: Dec. 30, 2013

(65) Prior Publication Data

US 2015/0185133 A1 Jul. 2, 2015

(51) Int. Cl.
| | |
|---|---|
| *G01N 27/416* | (2006.01) |
| *G01N 17/02* | (2006.01) |
| *G01N 17/04* | (2006.01) |
| *G01N 33/24* | (2006.01) |
| *G01N 27/04* | (2006.01) |

(52) U.S. Cl.
CPC ................ *G01N 17/02* (2013.01); *G01N 17/04* (2013.01); *G01N 27/043* (2013.01); *G01N 33/24* (2013.01)

(58) Field of Classification Search
CPC .............................. G01N 17/02; G01N 17/04
See application file for complete search history.

(56) References Cited

U.S. PATENT DOCUMENTS

| | | | | |
|---|---|---|---|---|
| 2,454,952 A | * | 11/1948 | Starkey et al. | 204/412 |
| 2011/0259092 A1 | * | 10/2011 | Yu et al. | 73/86 |

OTHER PUBLICATIONS pp. 4-43 to 4-101 of the chapter entitled "Physical Constants of Inorganic Compounds" in the CRC Handbook of Chemistry and Physics, 88th edition, 2008, downloaded from http://image.sciencenet.cn/olddata/kexue.com.cn/upload/blog/file/2008/12/2008121510347360620.pdf on Aug. 5, 2015.*
"Corrosion Testing Newsletter", Issue 7, Jan. 2004, Cooper Testing Labs, Inc., 3 pages.*
Product literature for Model 263A potentiostat/galvanostat Princeton Applied Research, published Aug. 1, 2008.*
Product literature for PowerCORR Corrosion Measurement Software Princeton Applied Research believed published Mar. 10, 2004.*

* cited by examiner

*Primary Examiner* — Alexander Noguerola
(74) *Attorney, Agent, or Firm* — Trego, Hines & Ladenheim, PLLC; Brandon C. Trego

(57) ABSTRACT

An apparatus and method for assessing subgrade corrosion is disclosed. The apparatus is configured to assess soil corrosivity and subgrade corrosion of a structure without disturbing the site where the structure resides and includes a probe having a plurality of electrodes and sensors configured to conduct environmental and corrosion measurements at the site, and a controller having a potentiostat contained therein to determine a corrosion rate at the site, wherein the corrosion rate provides an indicator of the amount of corrosion of the structure over time.

14 Claims, 7 Drawing Sheets

APPARATUS AND METHOD FOR ASSESSING SUBGRADE CORROSION

BACKGROUND OF THE INVENTION

This application relates to an apparatus and method for assessing subgrade corrosion and, more particularly, to an apparatus and its use in determining corrosion at a specified site.

The power industry has been installing structures in direct contact with soil for more than a century and many of these structures have become unstable due to corrosion damage on their foundations. Inspection of these structures requires extensive equipment and manpower to first stabilize the structure and then excavate for a direct assessment. The issue is that many structures are buried to a depth of ten feet or more and have significant side loads which may cause them to topple without proper precautions. The volume of soil to be removed becomes extensive and open holes must be controlled to prevent accidents to personnel and the general public. Inspection crews can then consume massive amounts of time documenting the severity of damage and location in respect to groundline and usually utilities opt for repairs while the excavation is still open. This process limits productivity, becomes extremely expensive and consumes operational budgets due to inefficiencies.

Traditionally utilities estimated corrosion rates by periodically measuring corrosion pitting on metal surfaces. This approach provides a crude estimation of corrosion rate and does not discriminate between the controls of the corrosion cell. In an effort to reduce these costs, contractors and utilities developed models relying on environmental factors to describe soil corrosivity. Unfortunately, the resulting accuracy estimates ranged between 50 and 78%. It was realized through laboratory testing that soil properties vary greatly and those models require development for specific geographic locations. This dictates that the process must be repeated randomly throughout the service territory and then validated through excavation and direct assessment.

Many factors have been found to govern and influence corrosion rates found on transmission structures. Some factors originate from the operation of the circuits and some result from utilities that share the same Rights of Way. Pipelines, chemical plants, mining operations and railroads are high on the list of commercial operations that impact the corrosion rates, but internal factors include circulating currents, unbalanced transformers and long line effects due to the shield wire.

Environmental factors that may describe corrosion rates are moisture, temperature, pH, soil resistivity and the oxidation state of the structure. Dissimilarities in moisture, aeration and temperature are also known factors that may accelerate the corrosion process.

As a result of these different stresses, several types of corrosion affect transmission structures and other components. These include:
General corrosion (uniform)
Pitting/crevice corrosion (localized)
Galvanic
Concentration cell (differential oxygen or moisture)
Metal ion cell
Fatigue
Microbial
Long line effects
Stray current (AC or DC)

Corrosion is an electrochemical process in which a transfer of electrons occurs during a chemical reaction. Electrochemical corrosion requires two processes to occur simultaneously, oxidation and reduction reactions. The oxidation reaction results in the liberation of electrons at the anodic site where the metal is corroding; the reduction reaction strips the electrons from the surfaces at the cathodic sites. The electrons in this circuit travel through the metal to the cathodic sites where they are consumed by electron acceptors (such as hydrogen ions to form a hydrogen atom). Charged ions migrate toward their respective sites in what is termed ionic conduction. There are anions with a negative charge and cations with a positive charge; the cations are categorized as electron acceptors while the anions are categorized as electron donors. See FIG. 1.

The ionic conduction to each site completes the circuit allowing corrosion to occur. The potential difference (voltage) between the two reaction sites is a measure of the driving force of the corrosion process. The current (amperage) between the sites is a measure of the rate at which the reactions are proceeding and may be considered the governing factor in the consumption rate of the material.

Common metals are typically found in nature as chemical compounds coupled with various oxides, chlorides, or sulfides. They seldom occur as pure metals. After they have been refined to an almost pure metal by man, nature wants to change them back to their original state in a process known as corrosion.

Environmental Factors

Five factors are considered to significantly influence corrosion rates in soil environments. These factors are hydrogen ion concentration (pH), soil resistivity, moisture, soil classification, and temperature. The research conducted in this project confirms that each factor does contribute to corrosion rates and provides a weighting factor that may guide the selection of sensor arrays to trend or monitor system degradation.

Hydrogen Ion Concentration (pH)

The hydrogen ion concentration of the soil or water in which a structure is located can affect the corrosiveness of the environment and the current required for cathodic protection. The hydrogen ion concentration is expressed in terms of pH. Stated mathematically, the pH value is the logarithm of the reciprocal of the hydrogen ion concentration. A change of one in pH value is equivalent to a change of ten times in concentration. pH values range from 0 to 14 with 0 to 7 being acidic, 7 being neutral, and 7 to 14 being alkaline.

pH readings may be taken with a meter in the field or on a separate soil sample. Most soils are slightly acidic and range from about 5.5 to about 6.5 in pH. More acidic soils, particularly those with a pH below 4, are highly conducive to corrosion activity. While localized pitting occurs quite often within soils that are relatively neutral, acidic soils will support more widespread or generalized corrosion.

Chemical corrosion is damage that can be attributed entirely to chemical attack without the additional effect of electron transfer. This type of corrosion often affects amphoteric materials such as zinc, tin, lead, aluminum, and beryllium that are sensitive to exposure to either extremely acidic or alkaline solutions. Aluminum, for example, corrodes under both low and high pH conditions as shown in FIG. 2. Amphoteric metals should only be used within a limited pH range due their sensitivity to chemical corrosion.

Examples of corrosive solutions that can promote chemical corrosion include incompletely cured concrete, acetic acid from volatilized wood or jute, waste products from industrial plants, and water with a large amount of dissolved oxygen.

Other compounds known to increase copper dissolution include pesticides, herbicides, fertilizers, and air borne pollution.

Redox

Redox is an indication of the dissolved oxygen levels in the electrolyte; it is only useful to determine if there are reduction reactions taking place at the time of testing. This limitation is significant because many of the reactions that take place in the soil are reversible. For example, after a rainfall the soil becomes saturated and water replaces the oxygen in the pore spaces. Once this happens the soil becomes an oxidizing soil until the soil drains and oxygen once again fills the pore spaces in the soil.

When activation polarization is the dominating factor, corrosion activity can be tracked by monitoring reduction reactions and soil moisture measurements should be made during testing to correlate the corrosion rates with the redox potentials.

Soil Resistivity

Soil consists of a mix of gravel, silt, loam, sand, water, and dissolved salts. Electrical current flows through the earth primarily as ion movement, and this ionic conduction is heavily influenced by the concentration and kinds of salts in the soil moisture. Ionic disassociation occurs when salts are dissolved, and it is the movement of these ions under the influence of electrical potential that enables the medium to conduct electricity.

Soil resistivity is the single most important characteristic used in the design of cathodic protection systems for buried structures. Protective current requirements, sacrificial anode outputs, and impressed current anode bed resistance are all dependent upon soil resistivity.

Soil corrosiveness is often classified on the basis of its resistivity, as shown in Table 1. In general, when soils have resistivity greater than approximately 50,000 Ωcm, corrosion is negligible and cathodic protection may not be needed.

TABLE 1

Corrosion Classification of Soil and Water

| Resistivity (Ω cm) | Corrosion Classification |
| --- | --- |
| 0-1000 | Extremely corrosive |
| 1000-2000 | Very corrosive |
| 2000-10,000 | Corrosive |
| Greater than 10,000 | Progressively less corrosive |

Moisture Gradients

Oxygen and water content are significant contributors in sub-grade corrosion. Soil moisture is usually measured with a dielectric capacitance-type meter and is expressed as a percentage of available pore volume. Alternately, soil moisture may be directly measured in the laboratory by drying and using gravimetric techniques. Research over the years has shown that corrosion rate levels are the highest between 15% and 40% moisture content by volume and drop off outside of this range. Water tables produce a moisture gradient that can change seasonally and plate the structure with dissolved salts causing aggressive corrosion rates to occur.

Chemical Compounds:

Chlorides, sulfates, nitrates, and many other chemical compounds act as a depolarizer causing protective passivation films to break down allowing corrosion to initiate. FIGS. 3A-3C illustrate the effects of moisture, temperature and salts on soil resistivity.

Soil Classification

Soils are classified by their percentage content of sand, loam and silt. Knowing the soil composition allows a corrosion engineer to understand how corrosive the environment may be. Table 2 shows the range of resistivities of several soil types.

TABLE 2

Examples of Soil Resistivities of Various Soil Compositions

| | Resistivity(Ω cm) | | |
| --- | --- | --- | --- |
| Medium | Minimum | Average | Maximum |
| Surface soils, loam, etc | $10^2$ | | $5 \times 10^3$ |
| Clay | $2 \times 10^2$ | | $10^4$ |
| Sand and gravel | $5 \times 10^3$ | | $10^5$ |
| Surface limestone | $10^4$ | | $10^6$ |
| Limestone | $5 \times 10^2$ | | $4 \times 10^5$ |
| Shale | $5 \times 10^2$ | | $10^4$ |
| Granites, basalts, etc | | $10^6$ | |
| Decomposed gneisses | $5 \times 10^3$ | | $5 \times 10^4$ |
| Slates, etc. | $10^3$ | | $10^4$ |
| Fresh water lakes | | $2 \times 10^4$ | $2 \times 10^7$ |
| Tap water | $10^3$ | | $5 \times 10^3$ |
| Sea water | 20 | $10^2$ | $2 \times 10^2$ |
| Pastoral, low hills, rich soil, typical of Dallas, Texas; Lincoln, Nebraska Areas | | $3 \times 10^3$ | |
| Flat country, marshy, densely wooded typical of Louisiana near Mississippi River | $2 \times 10^2$ | $10^4$ | |
| Pastoral, medium hills and forestation, typical of Maryland, Pennsylvania, New York, exclusive of mountainous territory and seacoasts | | $2 \times 10^4$ | |
| Rocky soil, steep hills, typical of New England | $10^3$ | $5 \times 10^4$ | $10^5$ |
| Sandy, dry, flat, typical of coastal country | $10^3$ | $5 \times 10^4$ | $5 \times 10^5$ |
| City, industrial areas | | $10^5$ | $10^6$ |
| Fills, ashes, cinders, brine, waste | $6 \times 10^2$ | $2.5 \times 10^3$ | $7 \times 10^3$ |
| Clay, shale, gumbo, loam | $3 \times 10^2$ | $4 \times 10^3$ | $2 \times 10^4$ |
| Same-with varying proportion of sand and gravel | $10^3$ | $1.5 \times 10^4$ | $10^5$ |
| Gravel, sand stones with little clay or loam, granite | $5 \times 10^4$ | $10^5$ | $10^6$ |

Temperature Gradients

Geographic locations can be categorized by levels of thermal and moisture content. The locations are generally characterized by an average condition so that the resulting corrosion rates will be representative throughout the year. At the thermal extremes, the polar and tundra regions have cold climates while desert, grasslands, and deciduous forests in savannas, and tropical rain forests have hot climates. Humidity levels vary from desert to rain forest with polar, tundra, boreal forest, prairie, and savanna having average conditions.

Accordingly, there is a need for a better way to assess sub-grade corrosion without excessive costs, labor, and dangers.

BRIEF SUMMARY OF THE INVENTION

These and other shortcomings of the prior art are addressed by the present invention, which provides a non-invasive screening technique that eliminates excessive labor and equipment costs by measuring the corrosion rates that may be sustained by the soil. This measurement of soil corrosivity may then be used to map out circuits where additional investigations should be made without the cost of stabilization and excavation.

According to one aspect of the invention, an apparatus configured to assess soil corrosivity and subgrade corrosion of a structure without disturbing the site where the structure resides includes a probe having a plurality of electrodes and sensors configured to conduct environmental and corrosion measurements at the site; and a controller having a potentiostat contained therein to determine a corrosion rate at the site, wherein the corrosion rate provides an indicator of the amount of corrosion of the structure over time.

According to another aspect of the invention, an apparatus configured to assess soil corrosivity and subgrade corrosion of a structure without disturbing the site where the structure resides includes a probe having a plurality of electrodes and sensors configured to measure environmental factors and corrosion rates at the site, and a controller having a data acquisition module, microcontroller module, and poteniostat. The potentiostat scans the electrodes and sensors for corrosion rates, soil resistivity, REDOX, and pH values and logs the corrosion rates and environmental factors and other data into the data acquisition module. The data acquisition module transfers the data to an internal storage device or transmits the data to an external device.

According to another aspect of the invention, a method for assessing subgrade corrosion at a specified site includes the steps of providing an apparatus having a probe and a controller with a potentiostat contained therein. The method further includes the steps of pressing the probe into a soil at the site, using the controller to conduct a test of the site, using the potentiostat to scan electrodes and sensors of the probe to take environmental and corrosion rate measurements, and providing the measurements to a user to allow a user to set up a maintenance plan for structures located at the site.

BRIEF DESCRIPTION OF THE INVENTION

The subject matter that is regarded as the invention may be best understood by reference to the following description taken in conjunction with the accompanying drawing figures in which.

DETAILED DESCRIPTION OF THE INVENTION

Figure 1:
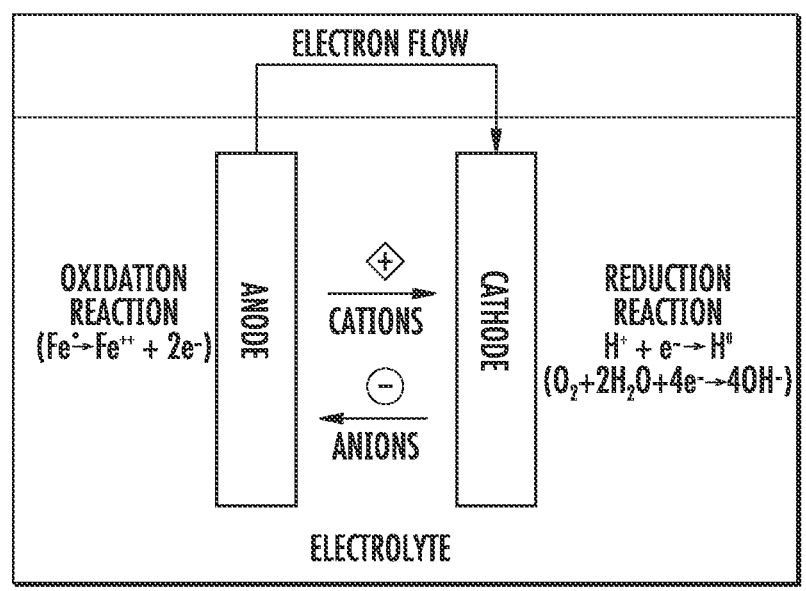
FIG. 1 illustrates an electrochemical process.
Figure 2:
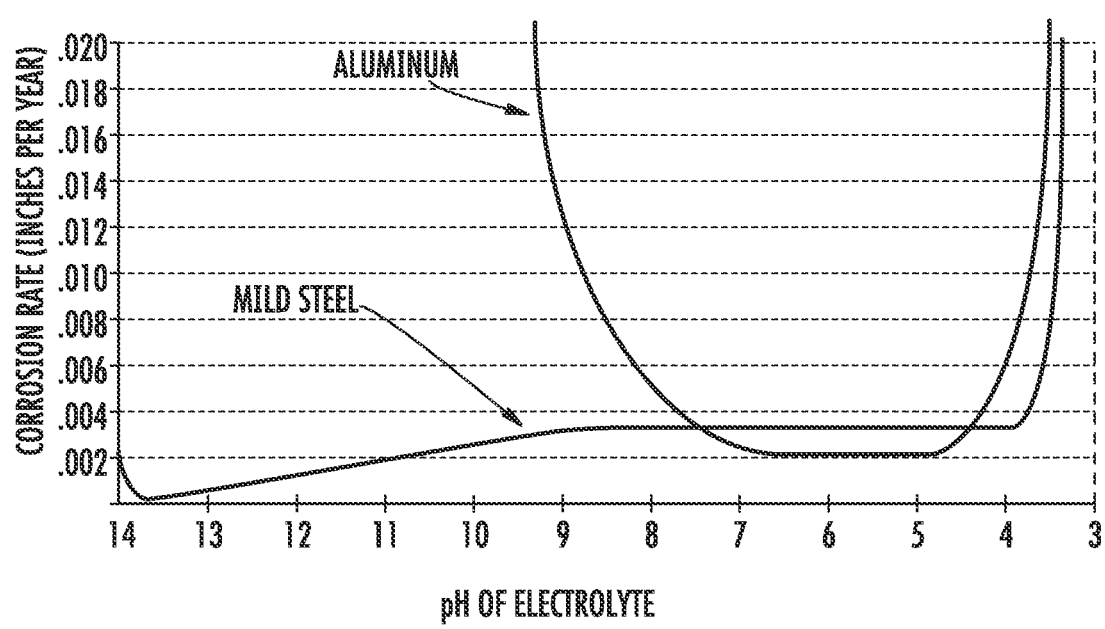
FIG. 2 illustrates corrosion with respect to ph for amphoteric materials.
Figure 3:
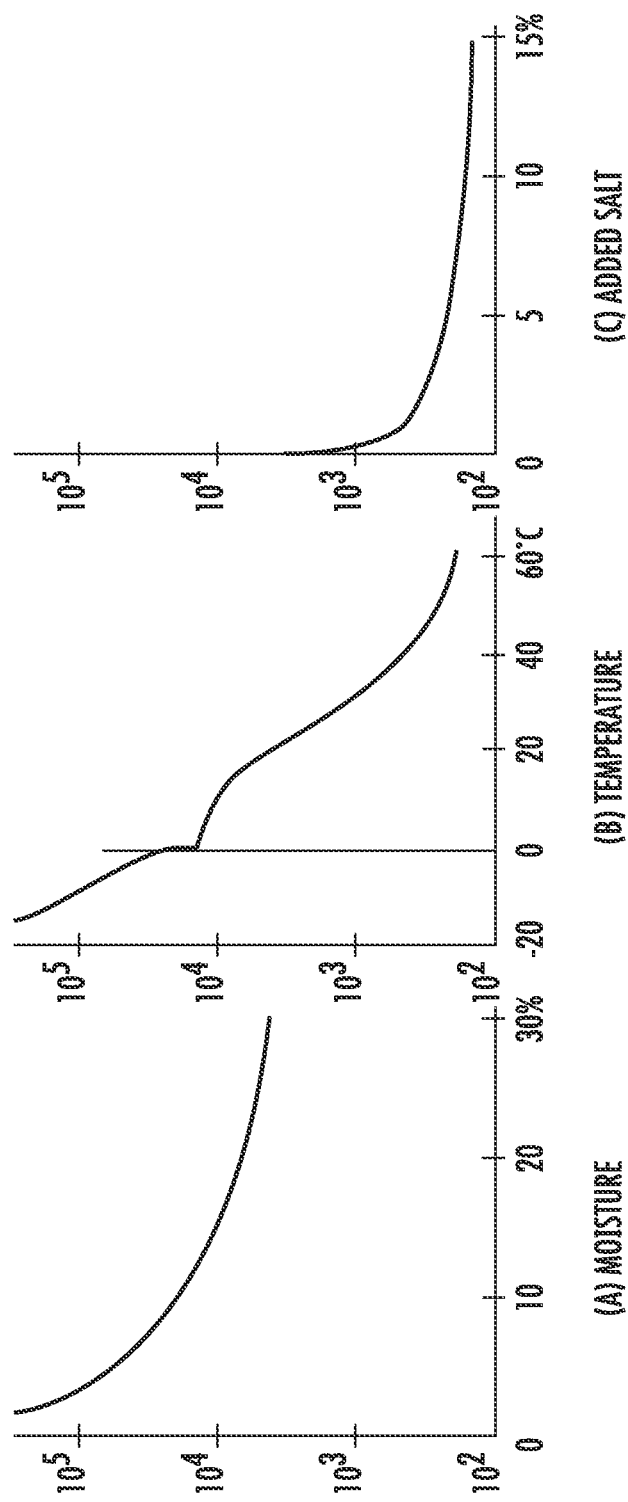
FIGS. 3A-3C illustrate resistivity of soil due to moisture, temperature, and salt.
Figure 4:
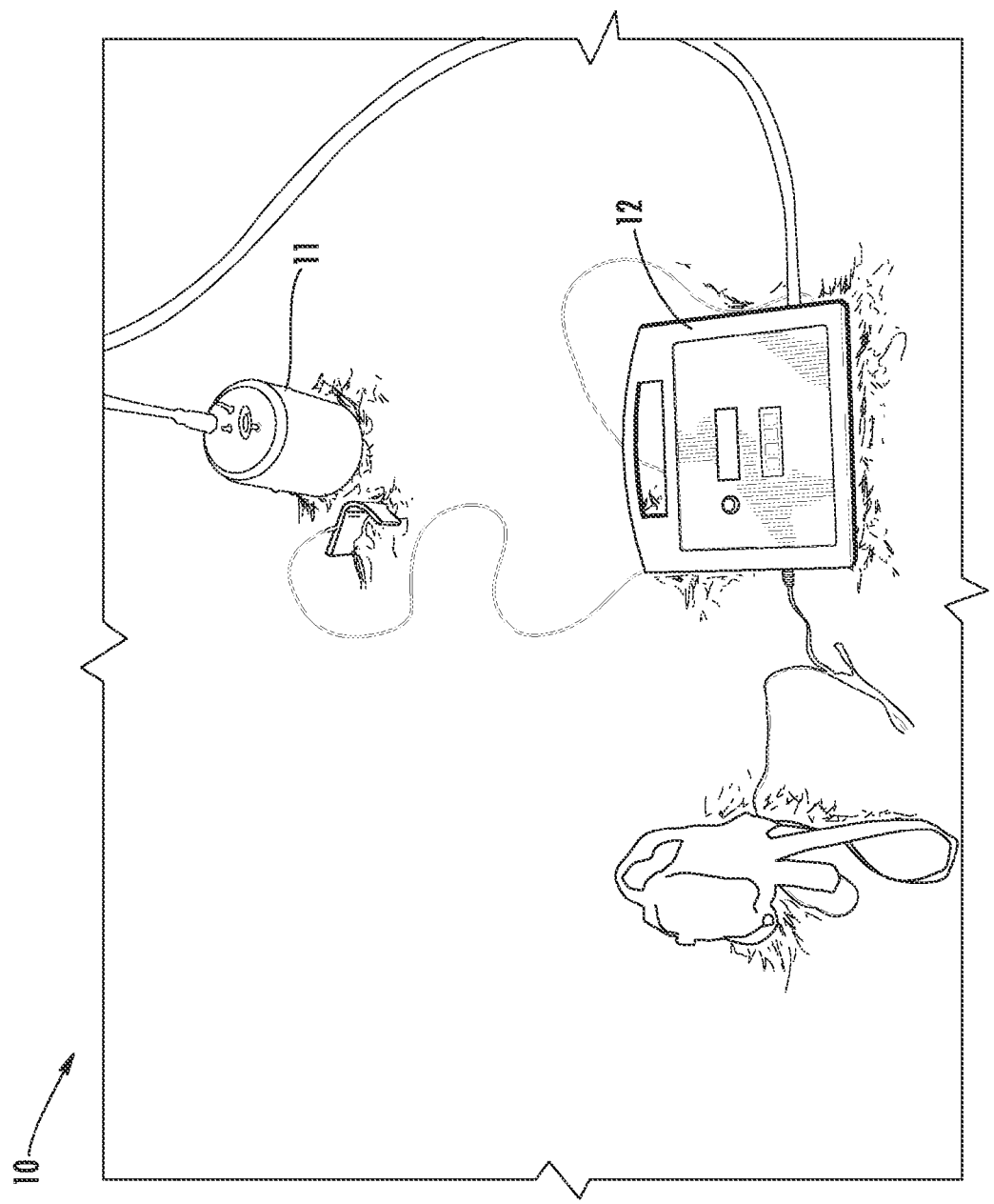
FIG. 4 shows an apparatus according to an embodiment of the invention.
Figure 5:
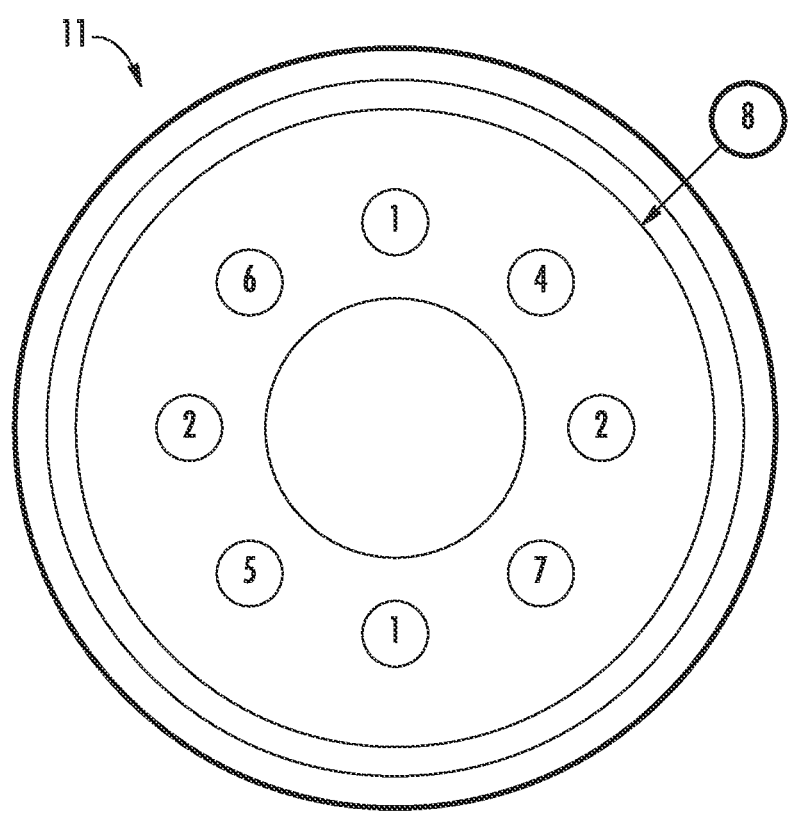
FIG. 5 shows a probe of the apparatus of FIG. 4.
Figure 6:
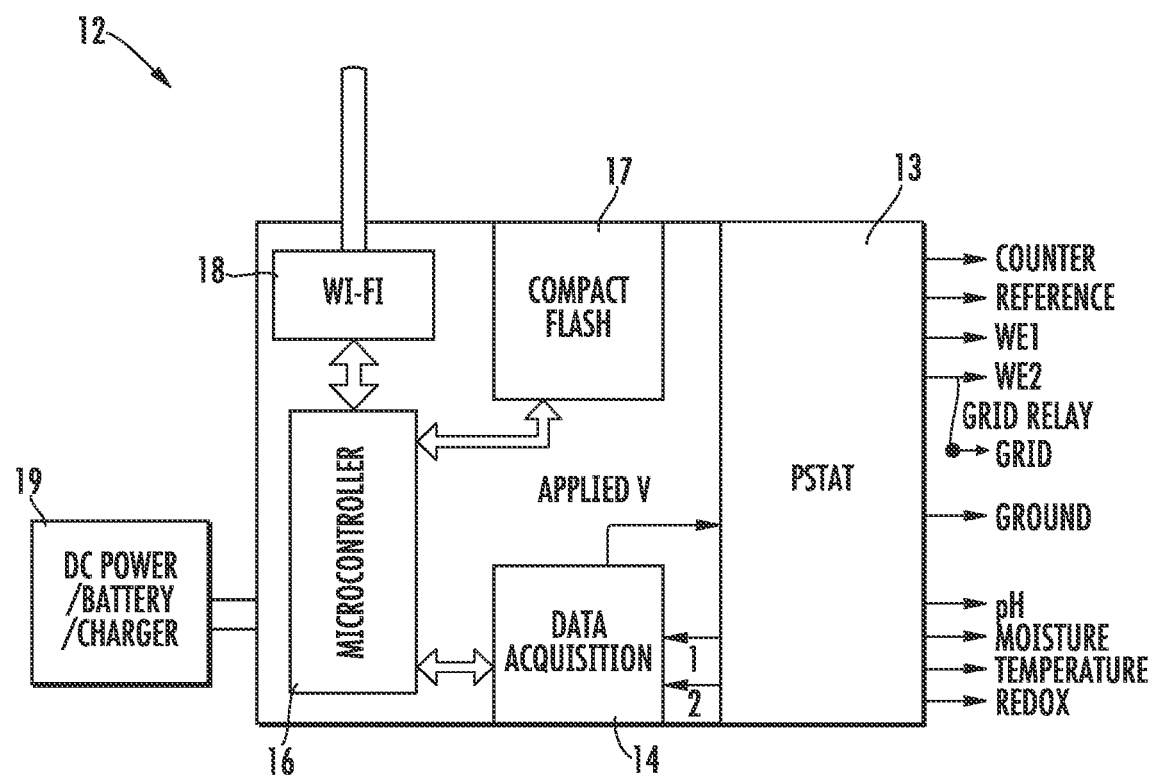
FIG. 6 shows a controller of the apparatus of FIG. 4.

Referring to the drawings, an apparatus in accordance with an embodiment of the invention is illustrated in FIGS. 4-6 and shown generally at reference numeral 10. The apparatus 10 includes a probe 11 and a controller 12 having a potentiostat 13 therein. The apparatus 10 is described in further detail below.

Quantifying the corrosion rate at a particular site is essential to understanding the progression of corrosion over time. The corrosion rate of a structure site will indicate if the soils are currently oxidizing or reducing by the severity of the corrosion level. If the corrosion rate is ½ mil or less per year we may consider the soil to be a reducing soil. Conversely, the corrosion rates can exceed those levels by a magnitude or more if there are strong depolarizers present in the soil or water.

Measurement of the redox level of the site will also provide some insight into the type of soil or condition of the soil at that point in time. Redox is an indication of the dissolved oxygen levels in the electrolyte; it is only useful to determine if there are reduction reactions taking place at the time of testing. This limitation is significant because many of the reactions that take place in the soil are reversible. For example, after a rainfall the soil becomes saturated and water replaces the oxygen in the pore spaces. Once this happens the soil becomes an oxidizing soil until the soil drains and oxygen once again fills the pore spaces in the soil. Soil moisture measurements should be made during testing to correlate the corrosion rates with the redox potentials.

Instantaneous corrosion testing can provide in situ corrosion rate measurements for the materials used in the construction of the structure at that particular site. Careful selection of pin materials can determine the corrosion rates for the galvanizing, copper grounds, and test coupons. Test coupons provide access to a structure or trend the influences of the environment around the structure.

Linear polarization testing can provide high production rates that are repeatable. The test method can be adapted to virtually any structure construction style such as lattice, anchors, or tubular structures.

In general, the apparatus 10 is based on the linear polarization resistance (LPR) technique, an electrochemical method of calculating corrosion rates by measuring the relationship between electrochemical potential and the electric current between electrodes. By using the LPR technique, the apparatus 10 can discriminate between general and stray current corrosion, accurately measures corrosion rate and, coupled with extensive soil and historical environmental data, enables accurate projections of component aging due to corrosion degradation.

The apparatus 10 dynamically measures soil corrosivity using probes, provides post processing, and archives the data for future analysis. The apparatus 10 enables transmission line maintenance crews to assess the condition of the foundations, discriminate between different types of corrosion, and develop cost-effective corrosion mitigation strategies to protect transmission assets, ensure public safety, and maintain service reliability. The apparatus 10 also supports fleet management of aging transmission line structures by enabling substation operators to assess the condition of a population of ground grids based on the electrical and environmental conditions that influence corrosion, and predict future corrosion progression and associated risk. With this knowledge and supporting analytical tools, transmission line asset managers would be able to make informed, risk-based asset management decisions regarding structures and optimize maintenance budgets.

The probe 11 is populated with a series of electrodes and sensors that are used to measure corrosion rates and soil conditions that exist near the structure foundation. The probe 11 contains three types of working electrodes that represent components used in the structure construction. The electrodes are copper representing the grounding system, zinc representing the galvanized protective coating and carbon steel representing the structural members. The sensors that are installed measure critical environmental factors such as moisture, tem perature, pH and the potentials of the working electrodes. The components of the probe 11 include:
1. Coupled and Uncoupled Working Electrodes (Carbon Steel)
2. Counter Electrodes (Titanium—soil resistance; Wenner method of measuring voltage drop as a function of current)
3. Permanent Reference Electrode
4. Temperature Sensor
5. Moisture Sensor
6. Redox Sensor (Iridium Oxide)
7. pH Sensor (Antimony)
8. Faraday Cage—(Copper)

One carbon steel working electrode is coupled to the structure to understand how the environment is affecting the structure and the other measures the corrosion rate of that site.

The controller 12 is powered by a battery 19 and uses the potentiostat 13 to make the corrosion rate measurements. A potentiostat can be thought of as a smart voltmeter or an automated soil resistivity box (Wenner) for measuring current flow as a function of potential. A potentiostat may be operated in potentiostatic or galvanostatic mode and as a two-electrode, three-electrode or four-electrode system with each configuration satisfying a specific need. Galvanostatic mode is when the current is changed and the voltage response is monitored and potentiostatic mode is when the voltage is changed with the current response being monitored.

Figure 7:
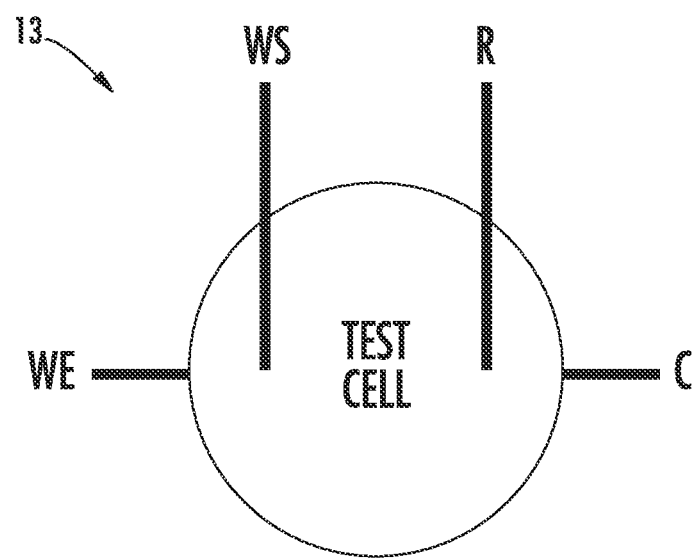
FIG. 7 illustrates a four electrode potentiostat used in the controller of FIG. 6.

A four electrode potentiostat is shown in FIG. 7 and includes:
WE Working Electrode (test sample)
WS Working Sense Electrode
C Counter Electrode (usually platinum, titanium or carbon)
R Reference Electrode (usually Silver/Silver Chloride, Saturated Calomel, Mercury/Mercury Oxide, Mercury/Mercury Sulfate, Copper/Copper Sulfate)

The potentiostat 13 makes the corrosion rate measurements by impressing a voltage on the working electrode and measuring the current response—this is converted into a polarization resistance and ultimately a corrosion rate (i.e., linear polarization resistance). The potentiostat is designed to scan the existing steel, copper and zinc pins for instantaneous corrosion rates but also the soil resistivity, REDOX and pH values and log the corrosion rates and environmental data for data transfer using a data acquisition module 14 and microcontroller module 16 and modeling of the transmission lines. The data may be stored on an SD card module 17 or other suitable storage device. At regular intervals the potentiostat communications protocols can be set to upload the data files through WiFi module 18 to a laptop or a cell modem.

The corrosion rates are a picture in time and the sensors allow an understanding of how often those conditions exist and where they exist once a circuit has been inspected. Population assessment may then be completed by grouping structures into categories of corrosion severity and then maintenance budgets may be set and programs implemented for repairs.

The foregoing has described an apparatus and its use in determining corrosion at a specified site. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

I claim:

1. An apparatus configured to assess soil corrosivity and subgrade corrosion of a structure without disturbing the site where the structure resides, comprising:
   (a) a probe having a plurality of electrodes and sensors configured to conduct environmental and corrosion measurements at the site;
   (b) a faraday cage around the probe to prevent electrical interference; and
   (c) a controller having a potentiostat contained therein to determine a corrosion rate at the site, wherein the corrosion rate provides an indicator of the amount of corrosion of the structure over time.

2. The apparatus according to claim 1, wherein the probe includes:
   (a) coupled and uncoupled working electrodes;
   (b) counter electrodes configured to measure soil resistance; and
   (c) a permanent reference electrode.

3. The apparatus according to claim 2, wherein the coupled and uncoupled working electrodes are carbon steel, and wherein the coupled working electrode is coupled to a structure to be tested to understand how the environment affects the structure and the uncoupled working electrode measures the corrosion rate of the site where the structure is located.

4. The apparatus according to claim 2, wherein the reference electrode is a material selected from the group Silver/Silver Chloride, Saturated Calomel, Mercury/Mercury Oxide, Mercury/Mercury Sulfate, and Copper/Copper Sulfate.

5. The apparatus according to claim 2, wherein the potentiostat makes corrosion rate measurements by impressing a voltage on the uncoupled working electrode and measuring the current response.

6. The apparatus according to claim 1, wherein the probe includes:
   (a) a temperature sensor configured to measure temperature;
   (b) a moisture sensor configured to measure moisture;
   (c) a redox sensor configured to measure redox potentials; and
   (d) a pH sensor configured to measure pH.

7. An apparatus configured to assesss soil corrosivity and subgrade corrosion of a structure without disturbing the site where the structure resides, comprising:
   (a) a probe having a plurality of electrodes and sensors configured to measure environmental factors and corrosion rates at the site, the plurality of probes including coupled and uncoupled carbon steel working electrodes, wherein the coupled working electrode is coupled to a structure to be tested and the uncoupled working electrode measures a corrosion rate of the site where the structure is located;
   (b) a controller having a data acquisition module, microcontroller module, and poteniostat, wherein the potentiostat scans the electrodes and sensors for corrosion rates, soil resistivity, REDOX, and pH values and logs the corrosion rates and environmental factors and other data into the data acquisition module, and wherein the data acquisition module transfers the data to an internal storage device or transmits the data to an external device.

8. The apparatus according to claim 7, wherein the plurality of electrodes includes:
   (a) a copper electrode which mimics a grounding system;
   (b) a zinc electrode which mimics a galvanized protective coating; and (c) a carbon steel electrode which mimics a structural member.

9. The apparatus according to claim 7, wherein the plurality of sensors includes:
   (a) a moisture sensor configured to measure moisture of the soil at the site;
   (b) a temperature sensor configured to measure temperature of the soil at the site; and
   (c) a pH sensor to measure the pH of the soil at the site.

10. The apparatus according to claim 7, wherein the potentiostat may be operated in a potentostatic or galvanostatic mode.

11. The apparatus according to claim 10, wherein the potentostatic mode changes a voltage while a current response is being monitored.

12. The apparatus according to claim 10, wherein the galvanostatic mode changes a current while a voltage response is being monitored.

13. The apparatus according to claim 7, wherein the potentiostat may be operated as a two-electrode, three-electrode, or four-electrode system depending on the specific measurements needed.

14. A method for assessing subgrade corrosion at a specified site, comprising the steps of:
   (a) providing an apparatus having:
      (i) a probe having a faraday cage positioned around the probe to prevent electrical interference; and
      (ii) a controller with a potentiostat contained therein;
   (b) pressing the probe into a soil at the site;
   (c) using the controller to conduct a test of the site;
   (d) using the potentiostat to scan electrodes and sensors of the probe to take environmental and corrosion rate measurements; and
   (e) providing the measurements to a user to allow a user to set up a maintenance plan for structures located at the site.

* * * * *